United States Patent [19]

Tanaka et al.

[11] Patent Number: 5,104,504
[45] Date of Patent: Apr. 14, 1992

[54] METHOD FOR THE PREPARATION OF AN ALCOHOL FROM HYDROCARBON

[75] Inventors: Masato Tanaka; Toshiyasu Sakakura; Fujio Abe, all of Tsukuba, Japan

[73] Assignee: Agency of Industrial Science and Technology, Tokyo, Japan

[21] Appl. No.: 588,095

[22] Filed: Sep. 21, 1990

[30] Foreign Application Priority Data

Sep. 22, 1989 [JP] Japan .................................. 1-247767

[51] Int. Cl.⁵ ...................... C07C 29/00; C07C 37/00
[52] U.S. Cl. ................................................ 204/157.9
[58] Field of Search ............ 204/157.9, 157.85, 157.88

[56] References Cited

U.S. PATENT DOCUMENTS 4,522,932  6/1985  Mitchell, III ......................... 502/153
4,900,413  2/1990  Sakakura et al. ................. 204/157.9

FOREIGN PATENT DOCUMENTS 49-26210  3/1974  Japan ................................. 204/157.9
184816   11/1965  U.S.S.R. ............................ 204/157.9

Primary Examiner—John Niebling
Assistant Examiner—Steven P. Marquis
Attorney, Agent, or Firm—Wenderoth, Lind & Ponack

[57] ABSTRACT

A efficient photochemical method for the preparation of an alcohol compound, e.g., benzyl alcohol, from a non-olefin hydrocarbon compound, e.g., benzene, was proposed in which a mixture of the non-olefin hydrocarbon compound as the starting material and a hydrogen donor compound, which is a cycloalkane of 5 to 16 carbon atoms in a molecule, e.g., cyclooctane, or an aliphatic alcohol of up to 10 carbon atoms in a molecule, e.g., isopropyl alcohol, is irradiated with light under an atmosphere of carbon monoxide in the presence of a complex compound of rhodium or iridium, of which at least one of the ligands is preferably a monophosphine or bisphosphine compound. The method is advantageous in that the reaction can proceed under mild reaction conditions and that the amount of the aldehyde compound formed in the reaction mixture as a by-product is very small as compared with conventional methods so as to greatly facilitate isolation of the desired alcohol product from the reaction mixture.

12 Claims, No Drawings 5,104,504

METHOD FOR THE PREPARATION OF AN ALCOHOL FROM HYDROCARBON

BACKGROUND OF THE INVENTION

The present invention relates to a method for the preparation of an alcohol from a hydrocarbon compound as the starting material. More particularly, the invention relates to a method for the preparation of an alcohol by the photochemical direct reaction of a hydrocarbon compound and carbon monoxide in the presence of a transition metal complex compound as a catalyst in which the amount of the aldehyde compound produced as a by-product is greatly decreased.

As is well known, a large scale industrial process has been established for the preparation of an alcohol by the so-called oxo process utilizing the hydroformylation reaction of an olefin with carbon monoxide in the presence of a catalyst. This process, however, is economically not quite advantageous because the olefin compound as the starting material must be produced by the high-temperature pyrolysis of a paraffin compound which is a process of low selectivity consuming a large guantity of energy. Accordingly, it is eagerly desired to develop a process for the preparation of an alcohol directly even from a non-olefin hydrocarbon compound as the starting material without using any olefin compound as an intermediate. In this regard, oxidation of a hydrocarbon compound into an alcohol may be within possibility but this process is industrially not practicable due to the problem of difficulties encountered in the control of the successive oxidation reactions.

The inventors have previously proposed a method for the preparation of an alcohol and an aldehyde by the direct reaction of a hydrocarbon compound with carbon monoxide in the presence of a photocatalyst (see, for example, Japanese Patent Kokai 64-6222 and 64-6224). This prior art method, however, has a problem in the relatively low selectivity for the formation of the desired alcohol compound relative to the aldehyde.

SUMMARY OF THE INVENTION

The present invention accordingly has an object to provide a novel and industrially applicable method for the preparation of an alcohol compound even from a non-olefin hydrocarbon compound as the starting material by the direct reaction with carbon monoxide in the presence of a photocatalyst with a high selectivity for the formation of the desired alcohol relative to the aldehyde compound as an undesirable by-product to be freed from the disadvantage in the above described prior art method.

Thus, the method of the present invention for the preparation of an alcohol represented by the general formula RCH$_2$OH, in which R is a monovalent hydrocarbon group free from aliphatic unsaturation and aliphatic cyclic structure and unsubstituted or substituted with a substituent selected from the class consisting of alkoxy, acyloxy, carboalkoxy and cyano groups and halogen atoms, from a hydrocarbon compound as the starting material comprises the step of: irradiating, with light, a mixture of a hydrocarbon compound represented by the general formula RH, in which R has the same meaning as defined above, and a hydrogen donor compound under an atmosphere of carbon monoxide in the presence of a complex compound or a coordination compound consisting of an atom of a transition total element as the central atom and a plurality of ligands.

In particular, the transition metal element as the central atom is, preferably, iridium or rhodium and at least one of the ligands is a monophosphine compound represented by the general formula R$^1$$_3$P or a bisphosphine compound represented by the general formula R$^1$$_2$P-A-PR$^1$$_2$, in which each R$^1$ is, independently from the others, a monovalent hydrocarbon group selected from the class consisting of alkyl, aralkyl, cycloalkyl and aryl groups and A is a divalent group selected from the class consisting of alkylene, cycloalkylene, arylene, aralkylene and ferrocenylene groups. Further, the hydrogen donor compound is preferably a cycloalkane compound having from 5 to 16 carbon atoms in a molecule or an alcohol compound having up to 10 carbon atoms in a molecule.

DETAILED DESCRIPTION OF THE PREFERRED EMBODIMENTS

As is understood from the above given description, the most characteristic feature of the inventive method consists in the use of a hydrogen donor compound admixed with the starting hydrocarbon compound in the direct photochemical reaction thereof with carbon monoxide in the presence of a photocatalyst.

Various kinds of hydrocarbon compounds having no aliphatic unsaturation and cyclic structure can be used a the starting material in the inventive method including non-cyclic alkanes such as methane, ethane, propane, butane, pentane, hexane, heptane, octane, nonane, decane, eicosane and the like and aromatic hydrocarbons such as benzene, toluene, ethyl benzene, propyl benzene, decyl benzene, α-, m- and p-xylenes, naphthalene, α- and β-methyl naphthalenes, α- and β-hexyl naphthalenes, o-, m and p-dibutyl benzenes, anthracene, 9,10-dihexyl anthracene and the like.

These hydrocarbon compound can be substituted at least partly with substituent atoms or groups for the hydrogen atoms therein provided that no particular adverse influence is caused on the reaction with carbon monoxide. Examples of such a substituent group or atom include alkoxy, acyloxy, carboalkoxy and cyano groups and halogen atoms.

It is essential in the inventive method that the above described starting hydrocarbon compound is admixed with a hydrogen donor compound to form a reaction mixture. Examples of preferable hydrogen donor compounds include cycloalkane compounds having from 5 to 16 carbon atoms in a molecule such as cyclohexane cyclooctane, cyclododecane and the like and aliphatic alcohol compounds having up to 10 carbon atoms in a molecule such as ethyl alcohol, isopropyl alcohol, sec-butyl alcohol, cyclohexanol and the like. When an alcohol is used as the hydrogen donor compound, it is of course that the alcohol as the hydrogen donor is different from the alcohol as the desired product or the alcohol as the hydrogen donor should be a less expensive alcohol than the alcohol as the product from the economical standpoint.

The amount of the hydrogen donor compound in the reaction mixture is in the range from 0.05 to 20 moles or, preferably, in the range from 0.1 to 10 moles per mole of the starting hydrocarbon compound.

The reaction of the inventive method proceeds in the presence of a transition metal complex compound as a catalyst. The transition metal element giving the central atom of the complex compound is preferably a metallic element belonging to Group VIII of the periodic Table or, more preferably, rhodium or irridium. Rhodium is the most preferable transition metal element.

It is important in the inventive method that at least one of the ligands forming the complex compound with the above mentioned transition metal atom as the central atom is a monophosphine compound represented by the general formula $R^1_3P$ or a bisphosphine compound represented by the general formula $R^1_2P-A-PR^1_2$, in which each $R^1$ is, independently from the others, a monovalent hydrocarbon group selected from the class consisting of alkyl, aralkyl, cycloalkyl and aryl groups and A is a divalent group selected from the class consisting of alkylene, cycloalkylene, arylene, aralkylene and ferrocenylene groups. Though not particularly limitative, the number of the carbon atoms in the monovalent hydrocarbon group denoted by $R^1$ should not exceed 20. Aryl groups as the monovalent hydrocarbon group denoted by $R^1$ are less preferable than the alkyl, aralkyl and cycloalkyl groups bonded to the phosphorus atom at the non-aromatic carbon atom in respect of the catalytic activity.

Particular examples of preferable ligand compounds include trimethylphosphine, triethylphosphine, tributylphosphine, trioctylphosphine, tricyclohexylphosphine, tribenzylphosphine, 1,2 bis(dimethylphosphino)ethane, 1,4-bis(dimethylphosphino)butane, 1,2-bis(dibutylphosphino) ethane, 1,2-bis(dicyclohexylphosphino)ethane, $\alpha,\alpha'$-bis(dimethylphosphino)o-xylene, 1,2-bis(dimethylphosphino)cyclohexane and the like. Types of combination of the molecules of these ligand compounds with the transition metal atom are not particularly limitative provided that at least one molecule of these phosphine compounds is contained as the ligand in the molecule of the complex. Types of the complex compound accordingly include $RhCl(R^1_3P)_3$, $RhCl(CO)(R^1_3P)_2$, $RhBr(CO)(R^1_3P)_2$, $HRh(CO)(R^1_3P)_3$, $HRh(CO)_2(R^1_3P)_2$, $RhCl(CO)(R^1_2P-A-PR^1_2)$, $[RhCl(R_1{}^3P)_2]_2$, $IrCl(CO)(R^1_3P)_2$, $IrBr(CO)(R^1_3P)_2$, $IrH_5 (R^1_3P)_2$, $IrH_3 (CO)(R^1_3P)_2$, $IrCl(CO)(R^1_2P-A-PR^1_2)$, $Cp'RhH_2 (R^1_3P)$, $Cp'IrH_2(R^1_3P)$, $Co_2 (CO)_6 (R^1_3P)_2$, $CpCoI_2 (R^1_3P)$, $CoBr_2 (R^1_3P)_2$, $CoCl (R^1_3P)_3$, $CoH(N_2) (R^1_3P)_3$, $CoH_3 (R^1_3P)_3$, $CpCo(R^1_3P)_2$, $AcCo(CO)_3 (R^1_3P)$, $Fe(CO)_3 (R^1_3P)_2$, $Ru(CO)_3 (R^1_3P)_2$ and the like, in which $R^1$ and A each have the same meaning as defined before, Cp is a cyclopentadienyl group, Cp' is a pentamethylcyclopentadienyl group and Ac is an acetyl group. Instead of the use of a complex compound prepared in advance separately, similar catalytic effects can be obtained by the in situ formation of the complex by the reaction of a transition metal compound with a phosphine compound in the reaction mixture.

The amount of the complex compound as the catalyst in the reaction mixture should be in the range from 0.0001 to 100 mmoles or, preferably, from 0.001 to 10 mmoles per mole of the starting hydrocarbon compound.

The reaction of the inventive method proceeds under irradiation with light which can be in the ultraviolet or visible range of the wavelength. Suitable light source includes mercury lamps, xenon lamps and sun light emitting or including, at least partly, the light having a wavelength in the range from 300 to 800 nm. It is of course optional, if desired, that a filter or monochromator is used to restrict the wavelength range of the light or to use a monochromatic light. The wavelength of the light for irradiation of the reaction mixture has some influences on the selectivity of the reaction in respect of the relative yields of the position isomers produced from the starting hydrocarbon compound.

Although the reaction of the inventive method can proceed even at a temperature below 0° C., it is preferable that the reaction mixture is irradiated with light at a temperature in the range from 0° to 250° C. or, more preferably, from room temperature to 200° C. depending on the starting material in order to achieve a desirable rate and selectivity of the reaction. The pressure of carbon monoxide over the reaction mixture should be in the range from 0.1 to 300 kg/cm² or, preferably, from 0.5 to 100 kg/cm². When the pressure of carbon monoxide is too low, the reaction rate is undesirably decreased. An excessively high pressure of carbon monoxide is also detrimental against the rate of reaction as is sometimes the case with a complex compound as the catalyst in a catalytic reaction.

The reaction of the inventive method can proceed without using any solvent in the reaction mixture but it is optional according to need to use an organic solvent having less susceptibility to the carbonylation reaction than the starting material of the reaction.

After completion of the reaction, the alcohol compound as the desired product can be isolated by first removing the unreacted starting compounds by distillation or other known means and then fractioning the residue by distillation, recrystallization, chromatography or other known methods for purification.

As is understood from the above given description, various advantages can be obtained by the inventive method that an alcohol compound can be prepared directly from a paraffin or an aromatic hydrocarbon compound to provide an efficient industrial method for the manufacture of the alcohol, that the reaction can proceed even under mild reaction conditions at around room temperature under normal pressure, that the method provides an efficient process for the utilization of carbon monoxide produced in large quantities as a waste gas from ironworks and the like and that the amount of aldehydes formed as a by-product is small as compared with prior art methods so that the alcohol compound as the product can be relatively easily isolated from the reaction mixture at low costs.

In the following, the method of the present invention is described in more detail by way of examples.

EXAMPLE 1

Into a pyrex glass-made flask of 70 ml capacity were introduced 6.7 mg (0.021 mmole) of chlorocarbonylbis(trimethylphosphine)rhodium, 13.8 ml of isopropyl alcohol as a hydrogen donor compound and 16.2 ml of benzene as the starting hydrocarbon compound and the mixture was fully deaerated by twice repeating freezing and thawing. Thereafter, carbon monoxide was introduced into the flask under normal pressure by using a rubber balloon while the mixture in the flask was irradiated with light emitted from an immersion-type high-pressure mercury lamp at room temperature for 16.5 hours under agitation. The reaction mixture after completion of the reaction was analyzed gas chromatographically with $\beta$-methyl naphthalene as the internal standard to determine the amounts of benzyl alcohol, benzaldehyde and biphenyl corresponding to the molar yields of 3170%, 270% and 42%, respectively, based on the molar amount of the rhodium complex used as the catalyst. Besides the above, the reaction mixture contained 157 mg of hydrobenzoin.

EXAMPLE 2

The experimental procedure was substantially the same as in Example 1 except that the amount of benzene as the starting hydrocarbon compound was decreased to 12 ml while 13.8 ml of isopropyl alcohol were replaced with 18 ml of cyclooctane as the hydrogen donor compound. The result of the analysis of the reaction mixture after completion of the reaction was that the molar yields of benzyl alcohol, benzaldehyde and biphenyl were 6624%, 350% and 8%, respectively, based on the molar amount of the rhodium complex used as the catalyst. Small amounts of cyclooctane carbaldehyde and cyclooctanemethanol were detected in the reaction mixture.

COMPARATIVE EXAMPLE 1

The experimental procedure was substantially the same as in Example 1 or 2 except that the hydrogen donor compound was omitted and the amount of benzene was increased to 30 ml. The result of the analysis of the reaction mixture after completion of the reaction was that the molar yields of benzyl alcohol, benzaldehyde and biphenyl were 738%, 6517% and 215%, respectively, based on the molar amount of the rhodium complex used as the catalyst.

EXAMPLE 3

Experiment was conducted in a similar manner to Example 1 by using n-decane as the starting hydrocarbon compound and cyclooctane as the hydrogen donor compound. The result of the analysis of the reaction mixture after completion of the reaction was that the molar yields of 1-undecanol and 1-undecanal were 1336% and 273%, respectively, based on the molar amount of the rhodium complex used as the catalyst. The total molar yield of other isomers of undecanol was only 38% relative to the rhodium complex.

EXAMPLE 4

The same experimental procedure as in Example 3 was repeated except that the reaction mixture was irradiated with light emitted from the high-pressure mercury lamp through a filter having such a transmission characteristic that the transmittance was 10% or smaller at a wavelength of 325 nm or shorter and 50% at a wavelength of 350 nm. The reaction mixture after completion of the reaction contained position isomers of undecanol in a total molar yield of 472% based on the amount of the rhodium complex as the catalyst including 1-, 2 , 3 , 4- and 5-undecanols in a proportion of 8:44:17:15:16.

EXAMPLE 5

The experimental procedure was substantially the same as in Example excepting replacement of the benzene as the starting hydrocarbon compound with the same volume of toluene. The reaction mixture after completion of the reaction contained position isomers of methylbenzyl alcohol in a total molar yield of 6332% based on the amount of the rhodium complex used as the catalyst including o-, m- and p-methylbenzyl alcohols in a proportion of 3:60:37. 2-phenylethyl alcohol was not detected in the reaction mixture. Tolualdehyde was produced in a molar yield of 385% as a total value for the o-, m and p-isomers relative to the rhodium complex used as the catalyst.

EXAMPLE 6

The experimental procedure was just the same as in Example 1 excepting replacement of the rhodium complex compound as the catalyst with the same molar amount of chlorocarbonylbis(trimethylphosphino)iridium. The molar yields of benzyl alcohol and benzaldehyde were 92% and 8%, respectively, based on the amount of the iridium complex used as the catalyst.

What is claimed is:

1. A method for the preparation of an alcohol represented by the formula $RCH_2OH$, in which R is a monovalent hydrocarbon group free from aliphatic unsaturation and cycloaliphatic structure and unsubstituted or substituted with a substituent selected from the group consisting of alkoxy, acyloxy, carboalkoxy, cyano, and halogen, from a hydrocarbon of the formula RH, in which R is as defined above which comprises the step of:

irradiating, with light, a mixture of said hydrocarbon and a hydrogen donor compound which is an aliphatic alcohol having up to 10 carbon atoms, under an atmosphere of carbon monoxide in the presence of a complex compound consisting of a transition metal element as the central atom and a plurality ligands, as a catalyst.

2. The method for the preparation of an alcohol as claimed in claim 1 in which the aliphatic alcohol is selected from the group consisting of methyl alcohol, ethyl alcohol, isopropyl alcohol, sec-butyl alcohol and cyclohexyl alcohol.

3. The method for the preparation of an alcohol as claimed in claim 1 in which the transition metal element is an element belonging to Group VIII of the Periodic Table.

4. The method for the preparation of an alcohol as claimed in claim 3 in which the transition metal element belonging to Group VIII of the periodic Table is rhodium or iridium.

5. The method for the preparation of an alcohol as claimed in claim 4 in which the transition metal element belonging to Group VIII of the Periodic Table is rhodium.

6. The method for the preparation of an alcohol as claimed in claim 1 in which at least one of the ligands in the complex compound of a transition metal element is a monophosphine compound represented by the formula $R^1_3P$ or a bisphosphine compound represented by the formula $R^1_2P$-A-$PR^1_2$, in which each $R^1$ is, independently from the others, a monovalent hydrocarbon group selected from the group consisting of alkyl, aralkyl, cycloalkyl and aryl groups and A is a divalent group selected from the class consisting of alkylene, cycloalkylene, arylene, aralkylene, and ferrocenylene groups.

7. The method for the preparation of an alcohol as claimed in claim 6 in which the monovalent hydrocarbon group denoted by $R^1$ is selected from the group consisting of alkyl, aralkyl and cycloalkyl groups.

8. The method for the preparation of an alcohol as claimed in claim 1 in which the light has a wavelength in the range from 300 nm to 800 nm.

9. The method for the preparation of an alcohol as claimed in claim 1 in which the irradiation with light is performed at a temperature in the range from 0° C. to 250° C.

10. The method for the preparation of an alcohol as claimed in claim 1 in which the pressure of the atmosphere of carbon monoxide is in the range from 0.1 to 300 kg/cm$^2$.

11. The method for the preparation of an alcohol as claimed in claim 1 in which the amount of the hydrogen donor compound is in the range from 0.1 to 10 moles per mole of the hydrocarbon.

12. The method for the preparation of an alcohol as claimed in claim 1 in which the amount of the complex compound as a catalyst is in the range from 0.001 to 10 mmoles per mole of the hydrocarbon.

* * * * *